US007018357B2

(12) United States Patent
Emmons

(10) Patent No.: US 7,018,357 B2
(45) Date of Patent: Mar. 28, 2006

(54) EXTERNAL MIXER ASSEMBLY

(75) Inventor: Clifford L. Emmons, Oakville, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 20 days.

(21) Appl. No.: 10/085,150

(22) Filed: Feb. 27, 2002

(65) Prior Publication Data
US 2002/0179641 A1    Dec. 5, 2002

Related U.S. Application Data

(60) Provisional application No. 60/271,793, filed on Feb. 27, 2001.

(51) Int. Cl.
*A61M 37/00*    (2006.01)

(52) U.S. Cl. .................. 604/82; 604/191; 604/187; 222/134

(58) Field of Classification Search ............... 604/191, 604/82, 83, 187, 218, 236, 238, 266, 310, 604/311; 606/93, 213, 214, 215; 222/137, 222/142, 145.1, 321.6, 330, 386, 328, 566, 222/570, 575, 145.5; 239/423, 588, 304, 239/306, 432
See application file for complete search history.

(56) References Cited

U.S. PATENT DOCUMENTS

| 1,920,721 A | 8/1933 | Tirrell | |
|---|---|---|---|
| 1,948,388 A | 2/1934 | Liberson | 128/234 |
| 2,112,160 A | 1/1938 | Jonhson | 128/234 |
| 3,223,083 A | 12/1965 | Cobey | 128/92 |
| 3,236,418 A | 2/1966 | Dalle et al. | 222/135 |
| 3,467,096 A | 9/1969 | Horn | 128/218 |
| 3,552,394 A | 1/1971 | Horn | 728/218 |
| 3,738,535 A * | 6/1973 | Nicholls | 222/137 |
| 3,767,085 A | 10/1973 | Cannon et al. | 222/82 |
| 4,040,420 A | 8/1977 | Speer | 128/218 |
| 4,121,739 A | 10/1978 | Devaney et al. | 222/137 |
| 4,226,235 A | 10/1980 | Sarnoff et al. | 128/218 |

(Continued)

FOREIGN PATENT DOCUMENTS

DE    1962855    12/1969

(Continued)

OTHER PUBLICATIONS

PCT Search Report.

*Primary Examiner*—Cris Rodriguez

(57) ABSTRACT

An external mixer assembly is provided which externally mixes and delivers a first and a second component of a biological adhesive to tissues or organs for sealing wounds, stopping bleeding and the like. The first and second components are mixed immediately after exiting from separate outlet ports disposed in fluid communication with component reservoirs. In on embodiment, the external mixer assembly includes a housing having a housing head for enclosing therein a first reservoir containing the first component, and a second reservoir containing the second component. The housing further includes a discharge nozzle defining a longitudinal axis for enclosing therein a conduit assembly having a first and a second conduit in communication with the first and second reservoir, respectively. A deflector assembly is connected to the discharge nozzle. The deflector assembly includes a deflector plate to provide a space for initial mixing of the first and second components. The deflector plate is oriented in generally parallel juxtaposed relation distal to the distal face of the discharge nozzle. The first and second components are preferably fibrinogen and thrombin which intermix to form a fibrin sealant.

17 Claims, 2 Drawing Sheets

U.S. PATENT DOCUMENTS

| | | | | |
|---|---|---|---|---|
| 4,260,077 | A | 4/1981 | Schroeder | 222/137 |
| 4,359,049 | A | 11/1982 | Redl et al. | 128/218 |
| 4,465,476 | A | 8/1984 | Gahwiler | 604/191 |
| 4,594,073 | A | 6/1986 | Stine | 604/187 |
| 4,631,055 | A | 12/1986 | Redl et al. | 604/82 |
| 4,673,395 | A | 6/1987 | Phillips | 604/191 |
| 4,734,261 | A | 3/1988 | Koizumi et al. | 422/100 |
| 4,735,616 | A | 4/1988 | Eibl et al. | 604/191 |
| 4,826,048 | A | 5/1989 | Skorka et al. | 222/137 |
| 4,861,339 | A | 8/1989 | Jonischkeit | 604/118 |
| 4,874,368 | A | 10/1989 | Miller et al. | 604/82 |
| 4,902,281 | A | 2/1990 | Avoy | 604/191 |
| 4,978,336 | A | 12/1990 | Capozzi et al. | 604/82 |
| 4,979,942 | A | 12/1990 | Wolf et al. | 604/83 |
| 5,116,315 | A | 5/1992 | Capozzi et al. | 604/82 |
| 5,226,877 | A | 7/1993 | Epstein | 604/35 |
| 5,228,883 | A | 7/1993 | Blakely et al. | 604/232 |
| 5,289,949 | A | 3/1994 | Gentile | 222/137 |
| 5,290,259 | A | 3/1994 | Fischer | 604/218 |
| 5,332,124 | A | 7/1994 | Cancro et al. | 222/137 |
| 5,335,827 | A | 8/1994 | Gentile | 222/137 |
| 5,368,563 | A | 11/1994 | Lonneman et al. | 604/82 |
| 5,376,079 | A | 12/1994 | Holm | 604/191 |
| 5,409,465 | A | 4/1995 | Boggs et al. | 604/191 |
| 5,433,352 | A | 7/1995 | Ronvig | 222/391 |
| 5,464,396 | A | 11/1995 | Barta et al. | 604/191 |
| 5,474,540 | A | 12/1995 | Miller et al. | 604/191 |
| 5,505,704 | A | 4/1996 | Pawelka et al. | 604/191 |
| 5,520,658 | A | 5/1996 | Holm | 604/191 |
| 5,582,596 | A | 12/1996 | Fukunaga et al. | 604/191 |
| 5,643,206 | A | 7/1997 | Fischer | 604/82 |
| 5,665,067 | A | 9/1997 | Linder et al. | 604/82 |
| 5,740,965 | A | 4/1998 | Miyagi et al. | 239/423 |
| 5,848,750 | A * | 12/1998 | Schwab | 239/405 |
| 6,412,709 | B1 * | 7/2002 | Sugiura | 239/432 |
| 6,527,749 | B1 * | 3/2003 | Roby et al. | 604/191 |
| 6,620,125 | B1 * | 9/2003 | Redl | 604/83 |

FOREIGN PATENT DOCUMENTS

| | | |
|---|---|---|
| DE | 7925536 | 3/1980 |
| DE | 4223356 | 1/1994 |
| EP | 156098 | 12/1984 |
| EP | 424068 | 4/1991 |
| EP | 669100 | 2/1995 |
| EP | 0815802 | 1/1998 |
| EP | 0830900 | 3/1998 |
| EP | 0835667 | 4/1998 |
| EP | 0858776 | 8/1998 |
| FR | 2399861 | 3/1979 |
| FR | 2722104 | 7/1994 |
| WO | 9407420 | 4/1994 |
| WO | 9619940 | 7/1996 |
| WO | 9639212 | 12/1996 |
| WO | 9733633 | 9/1997 |
| WO | 9802098 | 1/1998 |
| WO | 9810703 | 3/1998 |
| WO | 9810704 | 3/1998 |
| WO | 9813094 | 4/1998 |
| WO | 9840115 | 9/1998 |
| WO | 9840167 | 9/1998 |
| WO | 0056221 | 9/2000 |

* cited by examiner

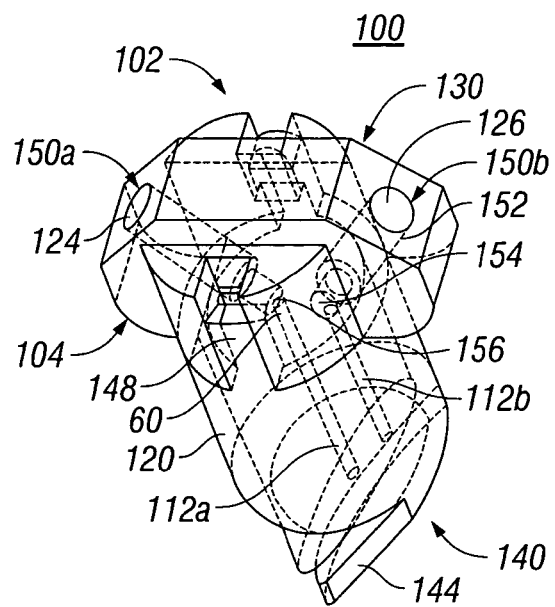
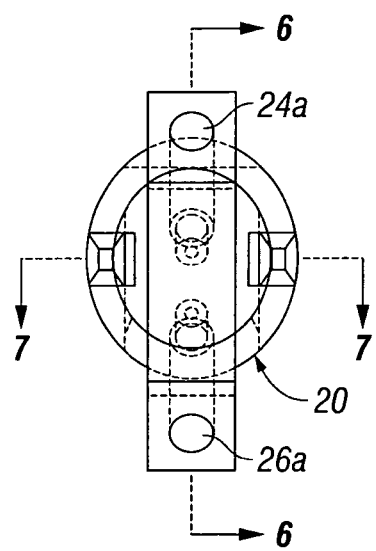
FIG. 4  FIG. 5
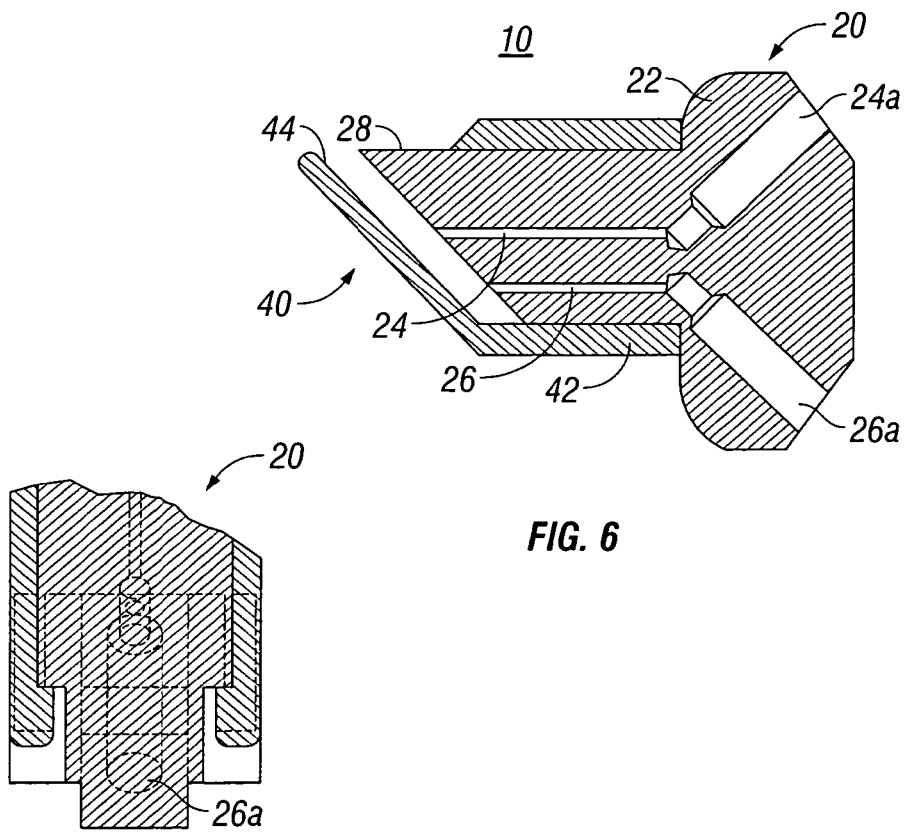
FIG. 6
FIG. 7

EXTERNAL MIXER ASSEMBLY

PRIORITY

This application claims priority under 35 U.S.C. §119(e) to a United States Provisional Application filed on Feb. 27, 2001 entitled "External Mixer" and having U.S. Provisional Application No. 60/271,793, the contents of which are hereby incorporated by reference.

BACKGROUND

1. Technical Field

The disclosure relates generally to a fluid delivery system for biological as well as synthetic sealants, hemostats and adhesives and, more particularly, to an external mixer assembly for mixing and delivering biological and/or synthetic biocompatible sealants, hemostats and adhesives to tissues or organs for sealing wounds, stopping bleeding and the like.

2. Description of Related Art

Biologically derived as well as synthetic sealants, hemostats and/or adhesives are used to treat wounds in instances where external dressings or sutures are not totally effective. A common treatment takes advantages of the rapid polymerization which occurs when a solution of proteomic clotting factors, such as fibrinogen, comes into contact with a solution of a proteomic catalyst, such as thrombin, to form a complex which acts as a hemostatic agent and as a tissue adhesive. This rapid polymerization typically commences within two seconds after the solutions initially contact one another, and it typically attains a soft set within ten seconds of contact. A common name for such a complex is fibrin glue or fibrin sealant.

The protein components of fibrinogen and thrombin which, together with a variety of known adjuvants, form a fibrin sealant are typically derived from human plasma and are subjected to virus elimination procedures. The components are typically individually dehydrated and stored in separate vials as sterile freeze-dried powders.

Because of the rapid polymerization upon intimate interaction of fibrinogen and thrombin, it is important to maintain these two blood proteins separate until applied at the application site. These protein solutions are generally delivered by fluid delivery systems, such as a dual syringe apparatus, where each solution is confined within a separate syringe prior to mixing.

One dual syringe apparatus for applying a fibrinogen-based tissue adhesive is disclosed in U.S. Pat. No. 4,359,049 to Redl et al. Redl et al. disclose a mechanism in which two standardized one-way syringes are held in a support having a common actuating means. The dispensing end of each syringe is inserted into a collection manifold where the two components are mixed. The components are then dispensed through a common needle capable of covering a limited area of the application site. It is often desirable or necessary to cover a broad area of a wound, either to stop bleeding, to fix tissue or to prevent infection. It is also desirable to prevent the two components from mixing within the dispensing device.

Further, all known devices for dispensing solutions of fibrinogen and thrombin require the addition of these proteins in powdered form to the body of the syringe. This makes the proteins susceptible to contamination by impurities which may enter the syringe body. Further still, the use of the syringe body to mix the proteins with water to create the protein solutions can cause the solutions to leak out from either the dispensing end of each syringe or the proximal end of the syringe body. Additionally, a dual syringe apparatus for the application of fibrinogen and thrombin solutions to an application site generally contains several parts, such as a syringe plunger, a "Y" manifold connector, a dispensing needle, a syringe holder, syringe needles, and conduits for transporting the solutions to the dispensing needle. Therefore, known fibrin sealant delivery systems or applicators, such as disclosed in U.S. patent to Redl et al. discussed above, and in U.S. Pat. No. 4,874,368 to Miller et al. and U.S. Pat. No. 4,979,942 to Wolf et al. are difficult to reuse. The replenishment of the protein components typically require removing a clip which couples the syringe plunger, removing the syringe plunger, detaching the syringes from the "Y" connector, removing the syringes from the holder, inserting new syringes, affixing the syringes to the "Y" connector, adding fibrinogen to one syringe and thrombin to another syringe, adding sterile water to each syringe, replacing the syringe plunger, replacing the plunger clip, and mixing the solutions. In an application where time is of the essence, such a lengthy replenishing process is impractical and cumbersome.

Furthermore, known fluid delivery systems for dispensing a biological adhesive require the manual exertion of a force on the protein components so they can be dispensed from the fluid delivery system. Typically, a manual force is exerted on the components by means of the plunger in the standard one-way syringe. This type of arrangement is shown in U.S. Pat. No. 4,359,049 discussed above, and U.S. Pat. No. 4,631,055 to Redl et al. Manually exerting a force on a plunger located at proximal end of the fluid delivery system can make the application of the adhesive difficult. For example, the user is unable to clearly view the application site when holding the fluid delivery system perpendicularly to the application site. Further, such an arrangement causes air to enter the syringes causing difficulty in exerting a force via the syringe plunger.

Thus, there is a need in the art for a fluid delivery system for applying a tissue adhesive wherein the adhesive covers a broad area of a wound, either to stop bleeding, to fix tissue or to prevent infection. There is also a need for a fluid delivery system wherein the adhesive components are not susceptible to contamination and the adhesive components are not intermixed within the fluid delivery system. Further, there is a need for a fluid delivery system wherein the component solutions are easily replenished. There is also a need for a fluid delivery system which is self-cleaning and reusable with different component solutions. Further, there is a need for a fluid delivery system which is inexpensive to manufacture for allowing the fluid delivery system to be disposed of after use. Additionally, there is a need for a fluid delivery system which avoids wasting adhesive solution and allows the application site to be clearly seen by the user when applying the component solutions perpendicular to the application site.

SUMMARY

A fluid delivery system is provided which is referred to herein as an external mixer assembly. The external mixer assembly externally mixes and delivers a first and a second component of a biological adhesive to tissues or organs for sealing wounds, stopping bleeding and the like. The first and second components are mixed immediately after exiting from separate outlet ports disposed in fluid communication with component reservoirs.

In a preferred embodiment, the external mixer assembly includes a housing having a housing head for enclosing therein a first reservoir containing the first component, and a second reservoir containing the second component. The housing further includes a discharge nozzle defining a longitudinal axis for enclosing therein a conduit assembly having a first and, a second conduit in communication with the first and second reservoir, respectively. A deflector assembly is connected to the discharge nozzle. The deflector assembly includes a deflector plate to provide a space for initial mixing of the first and second components. It is envisioned that the discharge nozzle and the deflector assembly may be formed into various configurations to provide adequate mixing and dispensing of the first and second components.

In one preferable embodiment, the discharge nozzle includes a distal face having an angular configuration. The deflector plate is oriented in generally parallel juxtaposed relation distal to the distal face of the discharge nozzle. It is envisioned, however, that the deflector plate is disposed in somewhat open or close relation with the distal face of the discharge nozzle depending upon the particular surgical needs. The size and configuration of the deflector plate may be varied. It is also contemplated that the distal face of the discharge nozzle may also be substantially perpendicular to the longitudinal axis of the discharge nozzle. The first and second components are preferably fibrinogen and thrombin which intermix to form a fibrin sealant.

BRIEF DESCRIPTION OF THE DRAWINGS

Various embodiments are described herein with reference to the drawings, wherein:

FIG. 4 is a phantom, perspective view of the embodiment illustrated in FIG. 1 having a housing head mounted thereon;

FIG. 5 is a perspective view of an external mixer assembly according to another embodiment of the present disclosure;

FIG. 6 is a cross-sectional view of the embodiment illustrated in FIG. 5, taken alone ling 6—6; and FIG. 7 is a cross-sectional view of the embodiment illustrated in FIG. 5, taken along the line 7—7.

DETAILED DESCRIPTION OF PREFERRED EMBODIMENTS

Figure 1:
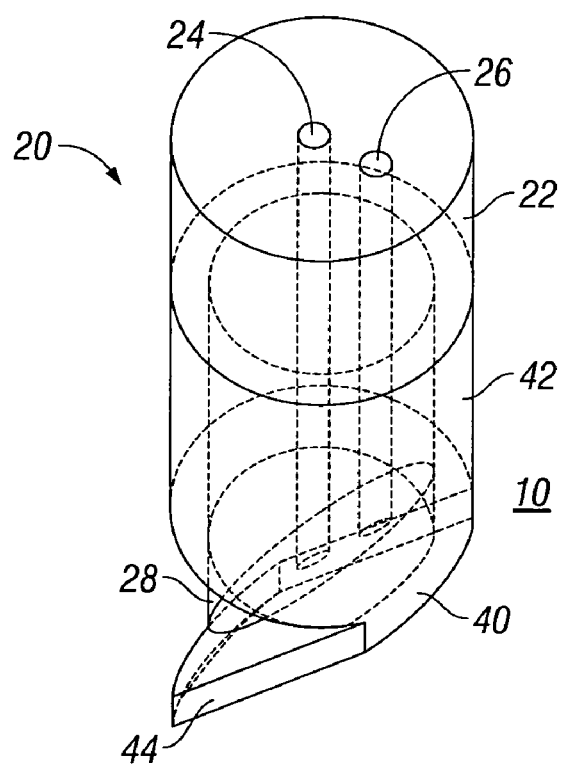
FIG. 1 is a phantom, perspective view of an external mixer assembly according to one embodiment of the present disclosure.
Figure 2:
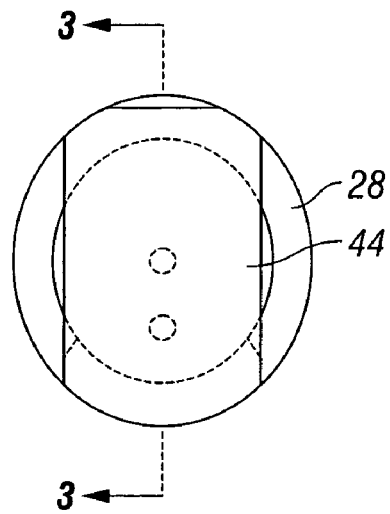
FIG. 2 is a rear, phantom view of the embodiment illustrated in FIG. 1, showing proximal end portions of the discharge nozzle.
Figure 3:
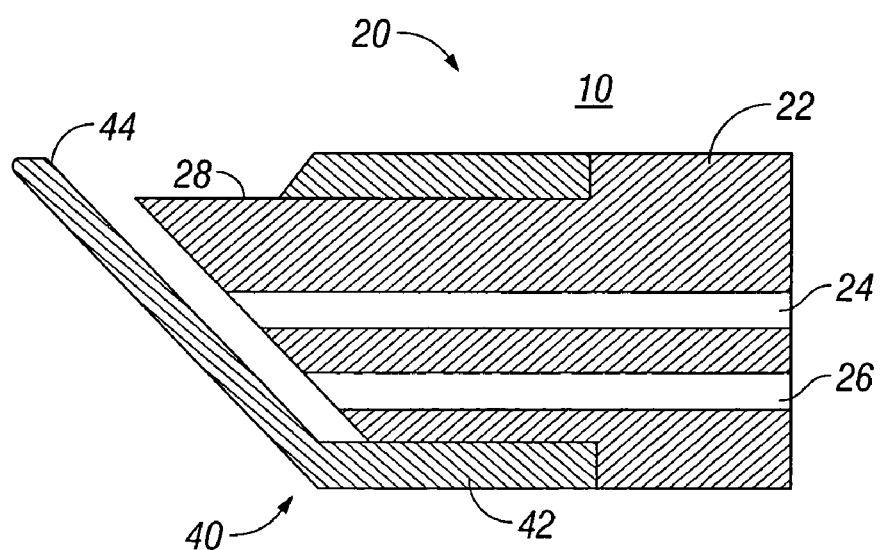
FIG. 3 is a cross-sectional view of the embodiment illustrated in FIG. 2, taken along the line 3—3.

Referring to FIGS. 1–4, an external mixer assembly according to one embodiment of the present disclosure is illustrated. The assembly designated generally by numeral 100 includes a housing 102 having a housing head 104 and a discharge nozzle 120 defining a longitudinal axis. While the housing head 104 is shown as being a particular shape, it is understood that other shapes that contribute to the ease of gripping and controlling the mixer assembly 100 may be used.

A nozzle tip 106 is provided at a distal end or face 108 of the discharge nozzle 120. The nozzle tip 106 includes two dispensing ports 110a, 110b where each dispensing port is in fluid communication with a respective conduit 112a, 112b of a conduit assembly 114 within the discharge nozzle 120 for dispensing biological components contained within housing head 104. Preferably, the biological components are a fibrinogen solution and a thrombin solution which intermix to form a fibrin sealant. It is to be understood, however, that other biological fluids may be substituted, depending upon the choice of mixture that is to be dispensed.

Housing 102 is preferably formed from molded housing half sections which are formed with internal partitions configured to properly align the internal components of the assembly 100 with respect to each other and to prevent movement of a first 150a and a second reservoir 150b each storing a biological component when the reservoirs 150a, 150b are fitted within reservoir conduits 124 and 126, as shown by FIG. 4. The main internal components of the assembly 100 include the conduit assembly 114 and a reservoir assembly 130. The two assemblies 114, 130 are interrelated with each other to dispense the biological components stored within the first and second reservoirs 150a, 150b via the two dispensing ports 110a, 110b.

The assembly 100 further includes a deflector assembly 140 connected to the housing 102 and the discharge nozzle 120. It is contemplated that holders 148 and 149 may be substituted by one or more other types of connection structure as known in the art. The deflector assembly 140 includes a cylindrical deflector housing 142 housing the discharge nozzle 120 when the deflector assembly 140 is connected to the housing 102 and the discharge nozzle 120.

A deflector plate 144 extends from a distal end of the deflector housing 142. The deflector plate 144 is displaced a relatively short distance from the distal face 108 of the discharge nozzle 120 to provide a space for initial mixing of the biological components dispensed from the two dispensing ports 110a, 110b. The deflector plate 144 is substantially parallel to the two dispensing ports 11a, 110b. Each of the two dispensing ports 110a, 110b is at an angle.

The deflector plate 144 is configured to facilitate both mixing and directing of the components. The deflector plate 144 is preferably oriented in general parallel relation with the distal face 108 of the discharge nozzle 120. It is contemplated that the deflector plate 144 may be disposed in open or close relation of some degree relative to the distal face 108 of the discharge nozzle 120 depending upon the specific application. It is also contemplated that the deflector plate 144 may be pivotably connected to the deflector housing 142 by a ratchet mechanism for pivoting and locking the deflector plate 144 in one of several positions with respect to the distal face 108 of the discharge nozzle 120 according to particular surgical needs.

The size and configuration of the deflector plate 144, and the gap there-between with the distal face 108 of the discharge nozzle 120, may be varied. The positions and orientations of the dispensing ports 110a, 110b, relative to the deflector plate 144, may also be varied depending upon surgical needs by changing the alignment of the conduits 112a, 112b with respect to the longitudinal axis of the discharge nozzle 120. That is, one or both of the conduits 112a, 112b may have one or more curves, the conduits 112a, 112b may be in divergent, convergent or parallel orientation with respect to each other, the conduits 112a, 112b may join in proximity to the distal face 108 of the discharge nozzle 120 to form one conduit, etc.

As known in the art, the first and second reservoirs 150a, 150b include a main body or a central throughbore 152 for storing the biological components. A plug 154 is used to vacuum seal the central throughbore 152 to prevent contamination of the biological components. The plug 154 preferably includes a silicon surface 156 capable of being penetrated by a syringe needle for adding a liquid, preferably sterile water, within the reservoirs 150a, 150b to intermix with the biological components to form protein solutions. The protein solutions are dispensed on the application site as discussed above. The conduit assembly 114 includes the two conduits 112a, 112b. Preferably, each conduit includes a beveled proximal tip 60 for penetrating a respective plug 154 of the first and second reservoirs 150a, 150b.

Preferably, the first and second reservoirs 150a, 150b are identical for encasing an equal volumetric amount of their respective protein solution as compared to the other reservoir. It is contemplated to provide a different color for each reservoir 150a, 150b to easily recognize the reservoir containing fibrinogen and the reservoir containing thrombin. It is further contemplated to provide a different shape for each reservoir and to change the shape of one or both of the reservoir conduits 124, 126 accordingly for the same purpose, i.e., to easily recognize the reservoir containing fibrinogen and the reservoir containing thrombin. However, the volumetric amount stored within the first reservoir 150a should be equal to the volumetric amount stored within the second reservoir 150b to maintain a pre-determined fibrinogen to thrombin solution ratio, which is typically a 1:1 ratio.

The first and second reservoirs 150a, 150b are preferably constructed from a flexible material and contain the first and second biological components, respectively. It is contemplated that the housing half sections are fully or partially transparent, as well as the first and second reservoirs 150a, 150b, for permitting a user to view the amount of solution and to determine if the solution has been sufficiently intermixed before being dispensed on the application site. It is further contemplated to provide calibration markings on the first 150a and second reservoir 150b.

Referring to FIGS. 5–7, an external mixer assembly according to an alternate embodiment of the present disclosure is shown and is designated generally by reference numeral 10. Generally, the external mixer assembly 10 is similar to the external mixer assembly 100 if the reservoir conduits 124 and 126 of the housing head 104 are integrally formed with the housing 102.

The external mixer assembly 10 includes a discharge nozzle 20 and a deflector assembly 40 connected to a distal end of the discharge nozzle 20. Discharge nozzle 20 includes a nozzle body 22 defining two longitudinal outlet ports 24 and 26 therein in fluid communication with their respective component reservoirs (not shown) fitted within reservoir conduits 24a and 26a. Nozzle body 22 includes a nozzle tip 28 at a distal end portion thereof, which is preferably configured as a cylinder having an angled distal face. It is provided that the component reservoirs may be similar to reservoirs 150a, 150b described above or different.

Deflector assembly 40 includes a connecting portion 42 at a proximal end thereof to connect to the distal end of the nozzle body 22. Deflector assembly 40 further includes a deflector plate 44 at a distal end thereof, which is displaced a relatively short distance from the distal face of the nozzle tip 28 to provide a space for initial mixing of the biological components. The deflector plate 44 is configured to facilitate both mixing and directing of the components. The deflector plate is preferably oriented in general parallel relation with the distal face of the nozzle tip 28.

It is contemplated that the deflector plate 44 may be disposed in open or close relation of some degree relative to the distal face of the nozzle tip 28 depending upon the specific application. It is also contemplated that the deflector plate 44 may be pivotably connected to the connecting portion 42 by a ratchet mechanism for pivoting and locking the deflector plate 44 in one of several positions with respect to the distal face of the nozzle tip 28 according to particular surgical needs.

The size and configuration of the deflector plate 44, and the gap there-between with the distal face of the nozzle tip 28, may be varied. The positions and orientations of the outlet ports 24 and 26, relative to the deflector plate 44, may also be varied depending upon surgical needs by changing the alignment of the outlet ports 24 and 26 with respect to the longitudinal axis of the discharge nozzle 20. That is, one or both of the outlet ports 24 and 26 may have one or more curves, the outlet ports 24 and 26 may be in divergent, convergent or parallel orientation with respect to each other, the outlet ports 24 and 26 may join in proximity to the distal face of the nozzle tip 28 to form one outlet port, etc. The external mixer assemblies according to the present disclosure are capable of applying a tissue adhesive where the adhesive covers a broad area of a wound, either to stop bleeding, to fix tissue or to prevent infection. The external mixer assemblies according to the present disclosure prevent the adhesive components from being susceptible to contamination and intermix the adhesive components externally.

Further, the external mixer assembly of the first embodiment allows for the component solutions to be easily replenished by removing the spent reservoirs from the reservoir conduits and replacing them with new reservoirs. Additionally, the external mixer assemblies according to the present disclosure avoid wasting adhesive solution and allow the application site to be clearly seen by the user when applying the component solutions perpendicular to the application site. It is contemplated that all the embodiments disclosed herein are disposable or have one or more disposable components. It is also contemplated that all the embodiments disclosed herein can be sterilized for re-use.

Therefore, it is understood that various modifications may be made to the embodiments disclosed herein. For example, while specific embodiments of the external mixer assembly have been described in detail, structures that perform substantially the same function in substantially the same way to achieve substantially the same result can also be used. Also, besides applying a fibrin sealant, the external mixer assembly can be used to perform human or veterinary surgical procedures including applying antiseptics, medication and other similar procedures. Therefore, the above description should not be construed as limiting, but merely as exemplifications of preferred embodiments. Those skilled in the art will envision other modifications within the scope and spirit of the claims appended thereto.

What is claimed is:

1. A fluid delivery system for dispensing a multicomponent biological adhesive having at least a first component and a second component, the system comprising:
    a housing configured to receive a plurality of reservoirs;
    a discharge nozzle housing a conduit assembly having a plurality of conduits with a proximal end thereof in respective fluid communication with separate of said reservoirs, a distal end of said conduits defining at least two exit openings, wherein each of said plurality of reservoirs includes a sealable opening configured for being penetrated by a proximal end of a respective one of said plurality of conduits; and
    a deflector assembly provided on said housing, said deflector assembly having a deflector plate substantially parallel with said at least two exit openings, said deflector plate displaced at a distance from a distal-most end of said housing and oriented to deflect said first and second components after exiting from said at least two exit openings.

2. The system of claim 1, wherein said deflector plate is oriented in general parallel relation to a distal face of said discharge nozzle.

3. The system of claim 1, wherein a first of said at least one exit opening and a second of said at least one exit opening are independent, such that said first and second components deflect and intermix external to said discharge nozzle against said deflector plate.

4. The system of claim 1, wherein said first component is a thrombin solution and said second component is a fibrinogen solution, whereby said biological adhesive is a fibrin sealant.

5. The system of claim 1, wherein said biological adhesive comprises a predetermined ratio of said first component to said second component.

6. The system of claim 1, wherein said housing includes a housing head for storing said plurality of reservoirs therein.

7. The system of claim 1, wherein the at least two exit openings are at an angle.

8. A fluid delivery system for dispensing a first and a second component of a biological adhesive, the system comprising:
   a housing configured to receive a plurality of reservoirs storing the first and second components;
   a nozzle assembly housed within a housing, said nozzle assembly having at least two dispensing conduits for dispensing the first component and the second component, wherein each of said plurality of reservoirs includes a sealable opening configured for being penetrated by a proximal end of the at least two dispensing conduits; and
   a deflector assembly connected to the nozzle assembly, said deflector assembly having a deflector plate to deflect said first and second components after being dispensed from a distal exit of a respective dispensing conduit of said at least two dispensing conduits, said deflector plate displaced at a distance from a distal-most end of said housing and being substantially parallel with said distal exits.

9. The system of claim 8, wherein said deflector plate is oriented in general parallel relation to a distal face of said nozzle assembly.

10. The system of claim 8, wherein a first of said at least one dispensing conduit and a second of said at least one dispensing conduit are independent, such that said first and second components deflect and intermix external to said nozzle assembly against said deflector plate.

11. The system of claim 8, wherein said first component is a thrombin solution and said second component is a fibrinogen solution, whereby said biological adhesive is a fibrin sealant.

12. The system of claim 8, wherein said biological adhesive comprises a predetermined ratio of said first component to said second component.

13. The system of claim 8, wherein said housing includes a housing head for storing a plurality of reservoirs therein, each of said plurality of reservoirs storing one of the first and the second components.

14. The system of claim 8, wherein the distal exits are at an angle.

15. A fluid delivery system for dispensing a multicomponent biological adhesive, the system comprising:
   a conduit assembly housed within a housing, said conduit assembly having two conduits each having an exit opening;
   a reservoir assembly having a first reservoir containing the first adhesive component and a second reservoir containing the second adhesive component, the first and second reservoirs being in fluid communication with a respective one of the two conduits, wherein the first and second reservoirs each include a sealable opening configured for being penetrated by a proximal end of the two conduits; and
   a deflector assembly having a deflector plate displaced at a distance from a distal end of said housing for receiving the first and the second adhesive components from the two conduits and deflecting the first and second adhesive components prior to dispensing to an application site, wherein said deflector plate is substantially parallel to each of said exit openings.

16. The system of claim 15, wherein said deflector plate is oriented in general parallel relation to a distal face of said conduit assembly.

17. The system of claim 15, wherein the exit openings are at an angle.

* * * * *